United States Patent [19]
Weber et al.

[11] Patent Number: 5,773,264
[45] Date of Patent: Jun. 30, 1998

[54] PROCESS FOR THE PRODUCTION OF 17 α-HYDROXY-3-METHOXY-8,14-SECO-1,3,5(10),9(11)ESTRATETRAEN-14-ONE BY REDUCTION OF THE CORRESPONDING 17-ONE COMPOUND

[75] Inventors: Alfred Weber; Mario Kennecke; Hans-Jorg Vidic, all of Berlin, Germany

[73] Assignee: Schering Aktiengesellschaft, Berlin, Germany

[21] Appl. No.: 313,063

[22] PCT Filed: Mar. 24, 1993

[86] PCT No.: PCT/DE93/00288

§ 371 Date: Sep. 26, 1994

§ 102(e) Date: Sep. 26, 1994

[87] PCT Pub. No.: WO93/20222

PCT Pub. Date: Oct. 14, 1993

[30] Foreign Application Priority Data

Mar. 28, 1992 [DE] Germany .................. 42 10 706.7

[51] Int. Cl.[6] .................. C12P 33/16; C12P 15/00
[52] U.S. Cl. .................. 435/127; 435/55; 435/280
[58] Field of Search .................. 435/55, 127, 280

[56] References Cited

U.S. PATENT DOCUMENTS

| | | | |
|---|---|---|---|
| 3,201,324 | 8/1965 | Hansen et al. | 195/51 |
| 3,481,974 | 12/1969 | Kraychy et al. | 260/488 |
| 3,616,225 | 10/1971 | Isono et al. | 195/51 R |
| 3,616,226 | 10/1971 | Isono et al. | 195/51 R |

FOREIGN PATENT DOCUMENTS

| | | |
|---|---|---|
| 1565986 | 2/1969 | France . |
| 300584 | 6/1992 | German Dem. Rep. . |

*Primary Examiner*—Sandra E. Saucier
*Attorney, Agent, or Firm*—Millen, White, Zelano, & Branigan, P.C.

[57] ABSTRACT

A process for the production of 17α-hydroxy-3-methoxy-8,14-seco-1,3,5 (10),9(11)estratetraen-14-one by fermentation of 3-methoxy-8,14-seco-1,3,5(10),9(11) -estratetraene-14,17-dione with a live culture of *Kloeckera magna* is described, which is characterized in that the substrate is reacted in the form of a solventless aqueous suspension with an average grain size of 0.2 to 5 μm.

1 Claim, No Drawings

PROCESS FOR THE PRODUCTION OF 17 α-HYDROXY-3-METHOXY-8,14-SECO-1,3,5(10),9(11)ESTRATETRAEN-14-ONE BY REDUCTION OF THE CORRESPONDING 17-ONE COMPOUND

The invention relates to a process for the production of 17α-hydroxy-3-methoxy-8,14-seco-1,3,5(10),9(11) estratetraen-14-one by fermentation of 3-methoxy-8,14-seco-1,3,5(10),9(11)-estratetraene-14,17-dione with a live culture of *Kloeckera magna*.

Such a process is already previously known from German Patent Application DE-A 17 68 513. It can be gathered from the embodiments of this patent application that this previously known process is performed in the way that the substrate is dissolved in ethanol and the obtained solution is reacted.

It has now been found that it is surprisingly possible to convert the substrate within a significantly shorter fermentation time while achieving significantly higher yields, if the substrate is added to the fermentation batch in the form of a solventless aqueous suspension with an average grain size of 0.2 to 5 μm.

The process according to the invention is performed under the fermentation conditions which are also used in the known microbiological conversions of substrates with *Kloeckera magna* cultures.

Under the culture conditions usually used for this microorganism, submerged cultures are cultivated in a suitable nutrient medium with aeration. Then, an aqueous suspension of 3-methoxy-8,14-seco-1,3,5(10),9(11)-estratetraene-14,17-dione is added to the culture and fermented until a maximum substrate conversion is achieved.

The aqueous suspension of 3-methoxy-8,14-seco-1,3,5 (10),9(11)-estratetraene-14,17-dione can be produced in a simple way by, for example, this substance being ground with two times to five times the amount of water with addition of a nonionic surfactant in a ball mill until it has an average grain size of 0.2 to 5 μm. Suitable surfactants are, for example, ethylene oxide adducts or fatty acid esters of polyglycols. As suitable surfactants, for example, the commercially available wetting agents such as Tegin(®), Tween (®) or Span(®) can be mentioned.

After completion of the fermentation, the culture is worked up in the usual way, for example, by it being extracted with a slightly water-soluble alcohol, ketone or ester, the extract being concentrated by evaporation and the obtained residue being purified by chromatography and/or crystallization.

The further processing of the obtained 17α-hydroxy-3-methoxy-8,14-seco-1,3,5(10),9(11)estratetraen-14-one to pharmacologically active steroids is known or takes place according to processes known in the art (German Patent Application DE-A 17 68 513).

The following embodiment is used to explain the process according to the invention in more detail.

EXAMPLE a) A 2 l Erlenmeyer with 1 l of sterile nutrient medium containing

| | |
|---|---|
| 0.1% | yeast extract |
| 0.1% | meat extract |
| 0.2% | tryptose |
| 1.0% | glucose | adjusted to pH 7.2 is inoculated with 5 ml of a suspension of a *Kloeckera magna* ATCC 20109 culture and shaken for 72 hours at 30° C. at 180 rpm.

b) A 5.5 $m^3$ fermenter with 5 $m^3$ sterile nutrient solution containing

| | |
|---|---|
| 5% | glucose |
| 2% | cornsteep liquor | adjusted to pH 5.4 is inoculated with 1l of the *Kloeckera magna* cultivation culture and incubated for 24 hours at 29° C. with aeration of 45 $m^3$ per hour and stirring at 60 rpm.

c) 100 kg of 3-methoxy-8,14-seco-1,3,5(10),9(11)-estratetraene-14,17-dione is ground in a Dynomühle [Dyno Mill] (Netzsch Company, Type KD 45) with glass bulbs, 400 l of water and 10 l of Tween 80 to a particle size of about 1 μm.

d) A 64 $m^3$ fermenter with 50 $m^3$ of sterile nutrient solution as indicated under b) is inoculated with 5 $m^3$ of *Kloeckera magna* preliminary culture and incubated with aeration of 500 $m^3$ per hour and stirring at 40 rpm at 29° C. for 6 hours.

Then the 3-methoxy-8,14-seco-1,3,5(10),9(11)-estratetraene-14,17-dione suspension produced according to c) is added to the culture and fermented for another 24 hours with stirring at 40 rpm and aeration of 500 $m^3$ per hour.

e) After completion of fermentation, the culture broth is extracted three times with methyl isobutyl ketone, the extract is concentrated by evaporation under vacuum at a maximum of 50° C. Then, a purification takes place by crystallization from ethanol.

80 kg of 17α-hydroxy-3-methoxy-8,14-seco-1,3,5(10),9 (11)estratetraen-14-one of melting point 102°–104° C. is obtained.

We claim:

1. A process for the production of 17α-hydroxy-3-methoxy-8,14-seco-1,3,5(10),9(11)-estratetraen-14-one, comprising fermenting 3-methoxy-8,14-seco-1,3,5(10), 9(11)-estratetraene-14,17-dione with a live culture of *Kloeckera magna* (ATCC-20109), wherein said substrate is added as an aqueous suspension, without an organic solvent, having an average grain size of 0.2–5 μm.

* * * * *